(12) United States Patent
Price et al.

(10) Patent No.: US 10,577,929 B2
(45) Date of Patent: Mar. 3, 2020

(54) METHOD TO IMPROVE MULTIVARIATE OPTICAL COMPUTING WITH AN ADD-ON INTEGRATED COMPUTATIONAL ELEMENT

(71) Applicant: HALLIBURTON ENERGY SERVICES, INC., Houston, TX (US)

(72) Inventors: James M. Price, Woodlands, TX (US); Bin Dai, Spring, TX (US); Christopher Michael Jones, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 470 days.

(21) Appl. No.: 15/537,342

(22) PCT Filed: Sep. 22, 2016

(86) PCT No.: PCT/US2016/053062
§ 371 (c)(1),
(2) Date: Jun. 16, 2017

(87) PCT Pub. No.: WO2018/056979
PCT Pub. Date: Mar. 29, 2018

(65) Prior Publication Data
US 2018/0320516 A1 Nov. 8, 2018

(51) Int. Cl.
*G01N 21/25* (2006.01)
*E21B 49/08* (2006.01)
(Continued)

(52) U.S. Cl.
CPC ............ *E21B 49/088* (2013.01); *E21B 44/00* (2013.01); *E21B 47/0002* (2013.01);
(Continued)

(58) Field of Classification Search
CPC ...... E21B 49/088; E21B 49/08; E21B 49/081; E21B 47/0002; E21B 44/00; E21B 2049/085; G01N 1/00
See application file for complete search history.

(56) References Cited

U.S. PATENT DOCUMENTS

| 2002/0090650 A1 | 7/2002 | Empedocles et al. |
| 2013/0284894 A1* | 10/2013 | Freese ............ G01N 21/17 250/208.2 |

(Continued)

OTHER PUBLICATIONS

International Search Report and Written Opinion from PCT/US2016/053062, dated Jun. 7, 2017.

*Primary Examiner* — Abdullahi Nur
(74) *Attorney, Agent, or Firm* — Gilliam IP PLLC

(57) ABSTRACT

A method is provided, including: forming an optical computing device having a first plurality of sensing elements selected to measure a characteristic of a sample, generating a transmission function from a first add-on integrated computational element (ICE), and evaluating, with a merit-function and the transmission function of the add-on ICE, a predictive performance of a modified optical computing device that includes the add-on ICE in addition to the first plurality of sensing elements. Also, modifying the first add-on ICE to improve the predictive performance of the modified optical computing device according to the merit-function and a modified transmission function of the add-on ICE.

20 Claims, 8 Drawing Sheets

(51) Int. Cl.
*E21B 44/00* (2006.01)
*E21B 47/00* (2012.01)
*G01N 1/00* (2006.01)

(52) U.S. Cl.
CPC ............ *E21B 49/08* (2013.01); *E21B 49/081* (2013.01); *E21B 2049/085* (2013.01); *G01N 1/00* (2013.01)

(56) References Cited

U.S. PATENT DOCUMENTS

| | | |
|---|---|---|
| 2015/0212232 A1 | 7/2015 | Perkins et al. |
| 2015/0234976 A1 | 8/2015 | Chen et al. |
| 2016/0003970 A1 | 1/2016 | Simcock et al. |
| 2016/0048627 A1 | 2/2016 | Perkins et al. |
| 2016/0054285 A1 | 2/2016 | Freese et al. |
| 2016/0076367 A1 | 3/2016 | Freese et al. |
| 2016/0130696 A1 | 5/2016 | Price et al. |
| 2016/0169794 A1 | 6/2016 | Powers et al. |
| 2016/0231459 A1 | 8/2016 | Perkins et al. |

* cited by examiner

METHOD TO IMPROVE MULTIVARIATE OPTICAL COMPUTING WITH AN ADD-ON INTEGRATED COMPUTATIONAL ELEMENT

BACKGROUND

In the field of oil and gas exploration and production, characterization of reservoir or wellbore fluid composition samples is desirable to determine the quality of a product or the condition of a container, a wellbore, or a pipeline, or to adjust and modify a drilling parameter. Existing sensors used in sample characterization often lose accuracy or sensitivity due to multiple factors, such as mechanical changes in the sensor setup or changes in the sampling conditions or fluid sample type. To correct for such effects, new re-calibration procedures are typically followed, which may ultimately result in the replacement of the sensor altogether. In such cases, this can require substantial re-testing of the replacement sensor, which can result in long time delays and costly expenses.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to those skilled in the art and having the benefit of this disclosure.

In the figures, elements or steps having the same or similar reference numerals have the same or similar description and configuration, unless stated otherwise.

DETAILED DESCRIPTION

Figure 1:
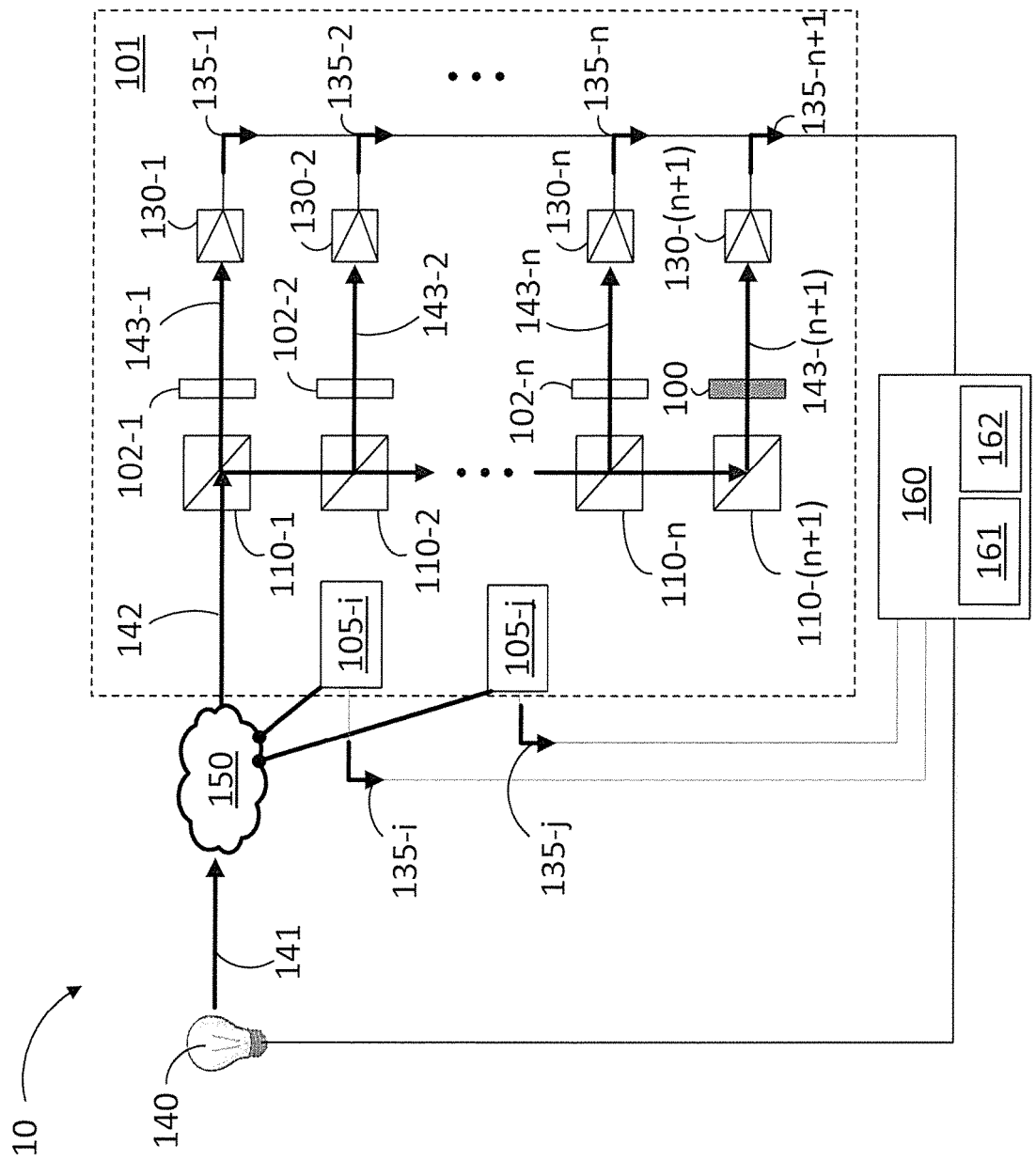
FIG. 1 illustrates a system for measuring a characteristic of a sample with an optical computing device including an add-on Integrated Computational Element (ICE).

The present disclosure relates to systems, devices and methods for enhancing the performance of an optical computing device in the measurement of a sample characteristic in the oil and gas exploration and production industry. According to the present disclosure, an additional or "add-on" integrated computational element (ICE) is included in an optical computing device having 'n' pre-existing sensing elements to enhance the performance of the optical computing device. Each of the 'n' pre-existing sensing elements may include an optical element such as a bandpass filter, a broadband filter, an ICE, or any other type of sensing element, such as a pressure sensor, a temperature sensor, a densitometer, and the like.

An ICE as disclosed herein is a processing element that optically interacts with a substance to determine quantitative and/or qualitative values of one or more physical or chemical properties of a substance to be analyzed. The ICE may comprise a multilayered interference element designed to operate over a continuum of wavelengths in the electromagnetic spectrum from the ultraviolet (UV, about 290 nm to about 400 nm), through the visible (VIS, about 400 nm to about 750 nm), through the near-infrared (NIR, about 750 nm to about 2500 nm), and to mid-infrared ranges (MIR, about 2500 nm to about 10,000 nm), or any sub-set of that region. Electromagnetic radiation that optically interacts with the ICE is modified to be readable by a detector such that an output of the detector can be correlated to the physical or chemical property or "characteristic" of the substance being analyzed.

As used herein, the term "characteristic" refers to a chemical, mechanical, or physical property of a substance. The characteristic of the substance may include a quantitative or qualitative value of one or more chemical constituents or compounds present therein, or any physical property associated therewith. Such chemical constituents and compounds may be alternately referred to as "analytes." Illustrative characteristics of a substance that can be monitored with the optical computing devices described herein can include chemical composition (e.g., identity and concentration in total or of individual components), phase presence (e.g., gas, oil, water, etc.), impurity content, ion content, pH, alkalinity, viscosity, density, ionic strength, total dissolved solids, salt content (e.g., salinity), porosity, opacity, bacteria content, total hardness, combinations thereof, state of matter (solid, liquid, gas, emulsion, mixtures, etc.), and the like.

As used herein, the term "electromagnetic radiation" refers to radio waves, microwave radiation, any radiation in the UV, VIS, NIR or MIR regions, X-ray radiation and gamma ray radiation.

As used herein, the term "optical computing device" refers to an optical device that is configured to receive an input of electromagnetic radiation, to interact the electromagnetic radiation with a substance and to produce an output of electromagnetic radiation from a processing element arranged within the optical computing device. In some embodiments, an optical computing device also includes a detector to generate an electronic signal indicative of a characteristic of the substance. The processing element may be, for example, an ICE, or a multivariate optical element (MOE). The electromagnetic radiation that optically interacts with the processing element is modified so as to be readable by a detector, such that an output of the detector can be correlated to a particular characteristic of the substance. The output of electromagnetic radiation from the processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As used herein, the term "optically interact" or variations thereof refers to the reflection, transmission, scattering, diffraction, or absorption of electromagnetic radiation either on, through or from one or more processing elements (i.e., ICE or MOE components) or a substance being analyzed by the processing elements. Accordingly, optically interacted light refers to electromagnetic radiation that has been reflected, transmitted, scattered, diffracted, or absorbed, emitted, or re-radiated, for example, using a processing element, but may also apply to interaction with a substance.

Methods consistent with embodiments disclosed herein include multivariate regression modeling of a fixed number 'n' of pre-existing sensing elements as a starting platform and subsequently designing at least one additional ICE to provide superior predictive performance when used in combination with the 'n' pre-existing sensing elements. In some embodiments, at least one of the 'n' pre-existing sensing elements includes an ICE associated with a regression vector related to the desired characteristic of the sample. The regression vector includes normalized weight values for each of a plurality of wavelengths across the spectral composition of a light that is going to be interacted with the sample, or that has been interacted with the sample. In some embodiments, the 'n' pre-existing sensing elements may include a plurality of ICEs, each ICE being associated with a spectral response of a basis function in a principal component analysis (PCA) decomposition of the desired characteristic of the sample.

In some embodiments, an additional, 'n+1,' ICE for the optical computing device is designed by using a response of a detector in the signal space (i.e., an electric signal such as a voltage or current), rather than looking at the spectral performance of the multilayer dielectric stack. This improves accuracy and sensitivity of the optical computing device. The added ICE ('n+1') provides greater flexibility for finding a better solution to the multivariate regression problem of measuring a desired characteristic of a sample compared to a single (or n-fold) ICE optical computing device. Moreover, optical computing devices as disclosed herein yield superior sensitivity and accuracy in a faster and more efficient manner, compared to single sensing element devices.

The methods disclosed herein include steps to modify an optical computing device that would yield 'n+1' sensing element responses selectively weighted based according to a multivariate regression model to predict the selected characteristic of interest. The 'n' pre-existing sensing elements may include any combination of optical and non-optical sensing elements. For example, the 'n' pre-existing elements may include some ICEs having a selected transmission in a first spectral domain and some ICEs having a selected transmission in a second spectral domain. Alternatively, the 'n' pre-existing sensing elements may include a different number of ICEs, narrow band filters designed for different spectral regions, and the like.

In a first embodiment, a method includes: forming an optical computing device having a first plurality of sensing elements selected to measure a characteristic of a sample, generating a transmission function from a first add-on integrated computational element (ICE), and evaluating, with a merit-function and the transmission function of the add-on ICE, a predictive performance of a modified optical computing device according to the characteristic of the sample, wherein the modified optical computing device includes the add-on ICE in addition to the first plurality of sensing elements. Also, and based upon the predictive performance of the modified optical computing device, modifying the first add-on ICE to improve the predictive performance of the optical computing device according to the merit-function and a modified transmission function of the add-on ICE.

In a second embodiment, a device includes a plurality of alternating layers of (at least) two materials having a different index of refraction. In the device, a thickness of each layer and a number of the plurality of alternating layers is selected according to an intensity of a sample light transmitted through the plurality of alternating layers, the sample light being obtained by interacting an illumination light with a sample. Also in the device, an intensity of the sample light transmitted through the plurality of alternating layers improves a merit function value for a measurement of a characteristic of the sample.

In yet another embodiment, a system includes a light source that generates an illumination light that optically interacts with a sample to form a sample light. In the system, a plurality of optical elements that direct a portion of the sample light to a corresponding plurality of sensing elements, wherein at least one of the plurality of sensing elements includes a plurality of alternating layers of two materials having a different index of refraction. In the system, an add-on integrated optical element includes a plurality of alternating layers of two materials having a different index of refraction. In the system, a thickness of each layer and a number of the plurality of alternating layers of the add-on integrated optical element are selected according to an add-on intensity of the sample light transmitted through the add-on integrated optical element. Accordingly, the additional intensity improves a merit function for measuring a characteristic of the sample.

FIG. 1 illustrates a system 10 for measuring a characteristic of a sample 150 with an optical computing device 101 including an add-on ICE 100. An optical source 140 provides an illumination light 141 to interact with sample 150, thus generating a sample light 142. Optical source 140 may be a broadband lamp, a laser, a light-emitting diode, or any other source of electromagnetic radiation. In some embodiments, sample light 142 may include fluorescence emitted photons or Raman shifted photons from sample 150.

Optical components 110-1, 110-2, . . . , 110-$n$ (hereinafter collectively referred to as optical components 110) separate sample light 142 into portions, each directed to one of sensing elements 102-1, 102-2, . . . , 102-$n$, respectively (hereinafter collectively referred to as sensing elements 102). It should be understood that at least some or all of optical components 110 may include any type of optical splitting and routing devices, such as beamsplitters, mirrors, dichroic filters, optical circulators, arrayed waveguide gratings (AWGs), and the like. Optical component $110_{n+1}$ directs a portion of sample light 142 onto add-on ICE 100.

System 10 also includes non-optical sensing elements 105-$i$ and 105-$j$ (hereinafter collectively referred to as non-optical sensing elements 105). Non-optical sensing elements 105 may include a temperature sensor, a pressure sensor, a densitometer, and the like. Non-optical sensing elements 105 provide signals 135-$i$ and 135-$j$ to a controller 160.

Optical elements 102 interact with the portions of sample light 142 to provide modified lights 143-1, 143-2, . . . , 143-$n$, respectively (hereinafter collectively referred to as modified lights 143). Add-on ICE 100 interacts with a portion of sample light 142 to form modified light $143_{n+1}$. A property of modified lights 143 is indicative of a desired characteristic of sample 150. In some embodiments, the property of modified lights 143 that is indicative of the characteristic of sample 150 may be an intensity, a polarization state, a phase, a wavelength, or any combination of the above.

Optical computing device 101 also includes detectors 130-1, 130-2, . . . , 130-$n$ (collectively referred hereinafter to as detectors 130) that receive modified lights 143-1, 143-2, . . . , 143-$n$, respectively. Detector $130_{n+1}$ receives modified light $143_{n+1}$. Detectors 130 provide sensing signals 135-1, 135-2, . . . , 135-$n$ (hereinafter collectively referred to as sensing signals 135) to controller 160. Detector $130_{n+1}$ provides sensing signal $143_{n+1}$ from add-on ICE 100. Sensing signals 135 may be electrical signals (e.g., a current or a voltage) associated with the spectral density distribution of sample light 142 in a linear or a nonlinear manner.

Controller 160 may include a processor 161 and a memory 162. Memory 162 stores data and commands which, when executed by processor 161, cause controller 160 to direct system 10 to perform steps in methods consistent with the present disclosure. Processor 161 may combine each of sensing signals 135-1, 135-2, . . . , 135-$n$ and $135_{n|1}$ according to commands stored in memory 162, to determine a selected characteristic of the sample.

Figure 2:
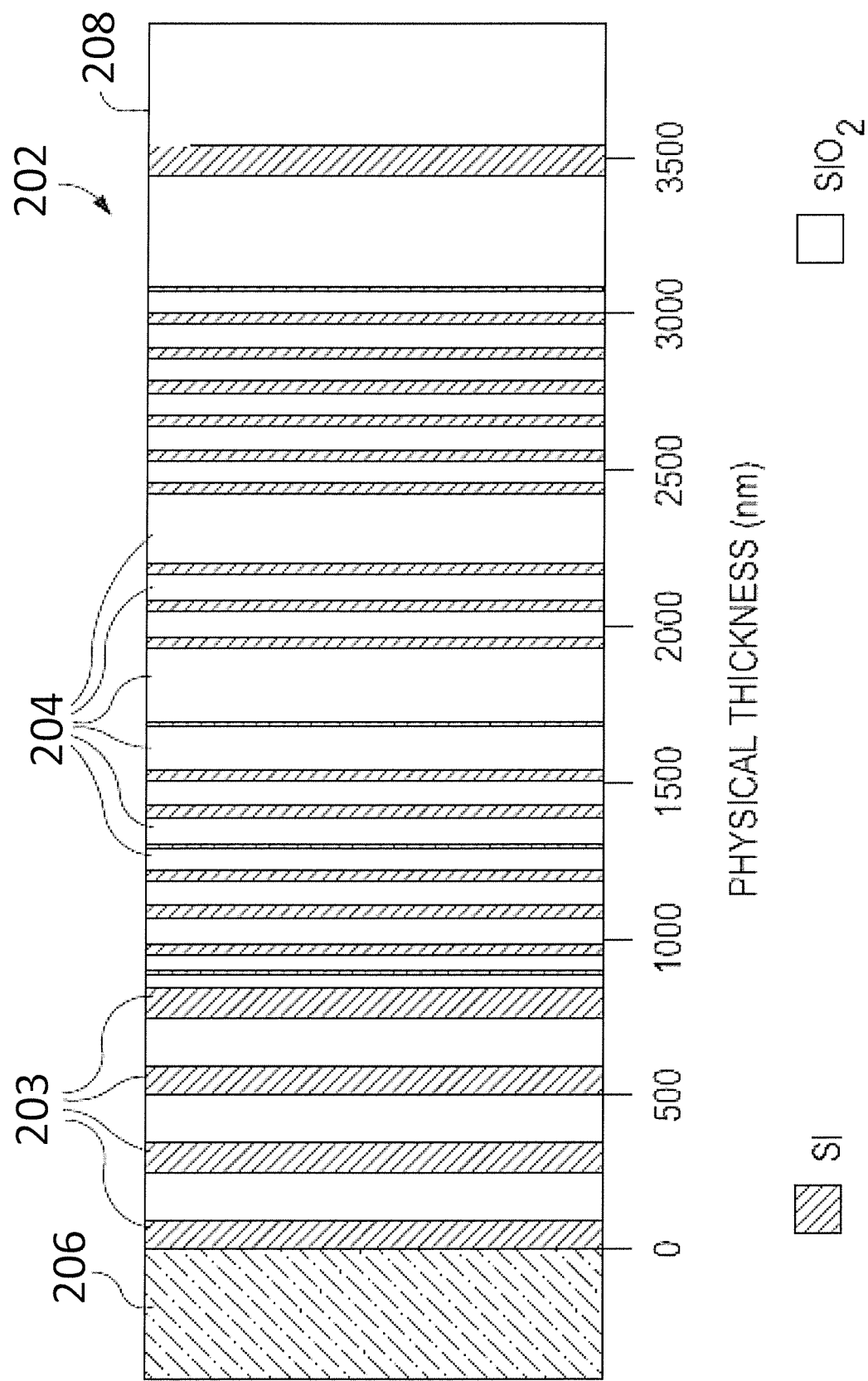
FIG. 2 illustrates a cross-sectional view of an exemplary ICE for adding on an optical computing device to improve the measurement of a characteristic of a sample.

FIG. 2 illustrates a cross-sectional view of an exemplary ICE 202 for adding on an optical computing device to improve the measurement of a characteristic of sample 150. ICE 202 may be similar to or the same as add-on ICE 100 of FIG. 1 and, therefore, may be used in optical computing device 101 of FIG. 1. As illustrated, ICE 202 may include a plurality of alternating layers 203 and 204, such as silicon (Si) and $SiO_2$ (quartz), respectively. In general, layers 203, and 204 include materials whose index of refraction is high and low, respectively. Other examples of materials for use in layers 203 and 204 might include niobia and niobium, germanium and germania, MgF, SiO, and other high and low index materials known in the art. Layers 203, 204 may be strategically deposited on an optical substrate 206. In some embodiments, the optical substrate 206 is BK-7 optical glass. In other embodiments, optical substrate 206 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

At the opposite end (e.g., opposite optical substrate 206 in FIG. 2), ICE 202 may include a layer 208 that is generally exposed to the environment of the device or installation, and may be able to detect a sample substance. The number of layers 203, 204 and the thickness of each layer 203, 204 are determined from the spectral attributes acquired from a spectroscopic analysis of a characteristic of the substance being analyzed using a conventional spectroscopic instrument. The spectrum of interest of a given characteristic typically includes any number of different wavelengths. It should be understood that ICE 202 in FIG. 2 does not in fact represent any particular characteristic of a given substance, but is provided for purposes of illustration only. Consequently, the number of layers 203, 204 and their relative thicknesses, as shown in FIG. 2, bear no correlation to any particular characteristic of a sample. Nor are layers 203, 204 and their relative thicknesses necessarily drawn to scale, and therefore should not be considered limiting of the present disclosure. Moreover, those skilled in the art will readily recognize that the materials that make up each layer 203, 204 (i.e., Si and $SiO_2$) may vary, depending on the application, cost of materials, and/or applicability of the material to the given substance being analyzed.

In some embodiments, the material of each layer 203, 204 can be doped or two or more materials can be combined to achieve the desired optical characteristic. In addition to solids, ICE 202 may also contain liquids and/or gases, optionally in combination with solids, in order to produce a desired optical characteristic. In the case of gases and liquids, ICE 202 can contain a corresponding vessel (not shown), which houses the gases or liquids. Exemplary variations of ICE 202 may also include holographic optical elements, gratings, piezoelectric, light pipe, and/or acousto-optic elements, for example, that can create transmission, reflection, and/or absorptive properties of interest.

Layers 203 and 204 exhibit different refractive indices. By properly selecting the materials of layers 203, 204 and their relative thickness and spacing, ICE 202 may be configured to selectively pass/reflect/refract predetermined fractions of electromagnetic radiation at different wavelengths. Each wavelength is given a predetermined weighting or loading factor. The thickness and spacing of layers 203, 204 may be determined using a variety of approximation methods from the spectrum of the characteristic or analyte of interest. These methods may include inverse Fourier transform (IFT) of the optical transmission spectrum and structuring ICE 100 as the physical representation of the IFT. The approximations convert the IFT into a structure based on known materials with constant refractive indices.

The weightings that layers 203, 204 of ICE 202 apply at each wavelength are set to the regression weightings described with respect to a known equation, or data, or spectral signature. When electromagnetic radiation interacts with a substance, unique physical and chemical information about the substance may be encoded in the electromagnetic radiation that is reflected from, transmitted through, or radiated from the substance. This information is often referred to as the spectral "fingerprint" of the substance. ICE 202 performs the dot product of the electromagnetic radiation received by the sample interacted light (e.g., sample light 142, cf. FIG. 1) and the wavelength dependent transmission function of ICE 202. The wavelength dependent transmission function of ICE 202 is dependent on the refractive index of the layer material, the number of layers 203, 204 and the layer thicknesses.

In some embodiments, the transmission function of ICE 202 is designed to mimic a desired regression vector derived from the solution to a linear multivariate problem targeting a specific component of the sample being analyzed. As a result, the output light intensity of ICE 202 (e.g., the intensity of modified light 143, cf. FIG. 1) is proportional a dot product of a transmission spectrum of the sample with the regression vector associated with the characteristic of interest. Accordingly, the output light intensity of ICE 202 is a direct indicator of a value of the characteristic of interest of the sample.

In some embodiments, the thickness and number of each layer 203 and 204 in ICE 202 are selected such that the resulting transmission spectrum of ICE 202 is similar to one of a plurality of basis functions in a principal component analysis (PCA) decomposition of the desired characteristic of a sample.

Designing ICE 202 may include a comparison of the transmission spectrum of ICE 202 with an optical pressure-volume and Temperature (PVT) database. The PVT-database includes spectra (i.e., transmittance spectra, absorbance spectra, reflectance spectra, fluorescence spectra, Raman spectra, and the like) of multiple samples with known values of the desired characteristic of the sample under known density, pressure and Temperature conditions. The predictive performance of ICE 202 may be evaluated in terms of accuracy and sensitivity for measuring the desired characteristic of the sample. A merit-based function such as a standard error of calibration (SEC), a root mean SEC (RMSEC), a sensitivity, an accuracy, or any combination of the above is used to determine the quality of a given ICE 202 design. For example, a SEC-based merit-function having a low value close to a global minimum may be desirable. In some embodiments, a sensitivity-based merit function having a high value close to a global maximum may be desirable.

While some embodiments of optical computing device 101 may use a single ICE to determine the selected characteristic of the sample, some embodiments may benefit from additional ICEs 202. The additional ICE 202 may include layers 203 and 204 selected according to a signal from a detector output (e.g., signal $135_{n+1}$ from detector $130_{n+1}$, cf. FIG. 1). More specifically, the number and thicknesses of layers 203 and 204 are determined such that signal $135_{n+1}$ improves (e.g., reduces or increases) a value of the merit-function associated with the desired characteristic of the sample when included in a multivariate linear regression algorithm (e.g., carried out by processor 161, cf. FIG. 1).

Figure 3:
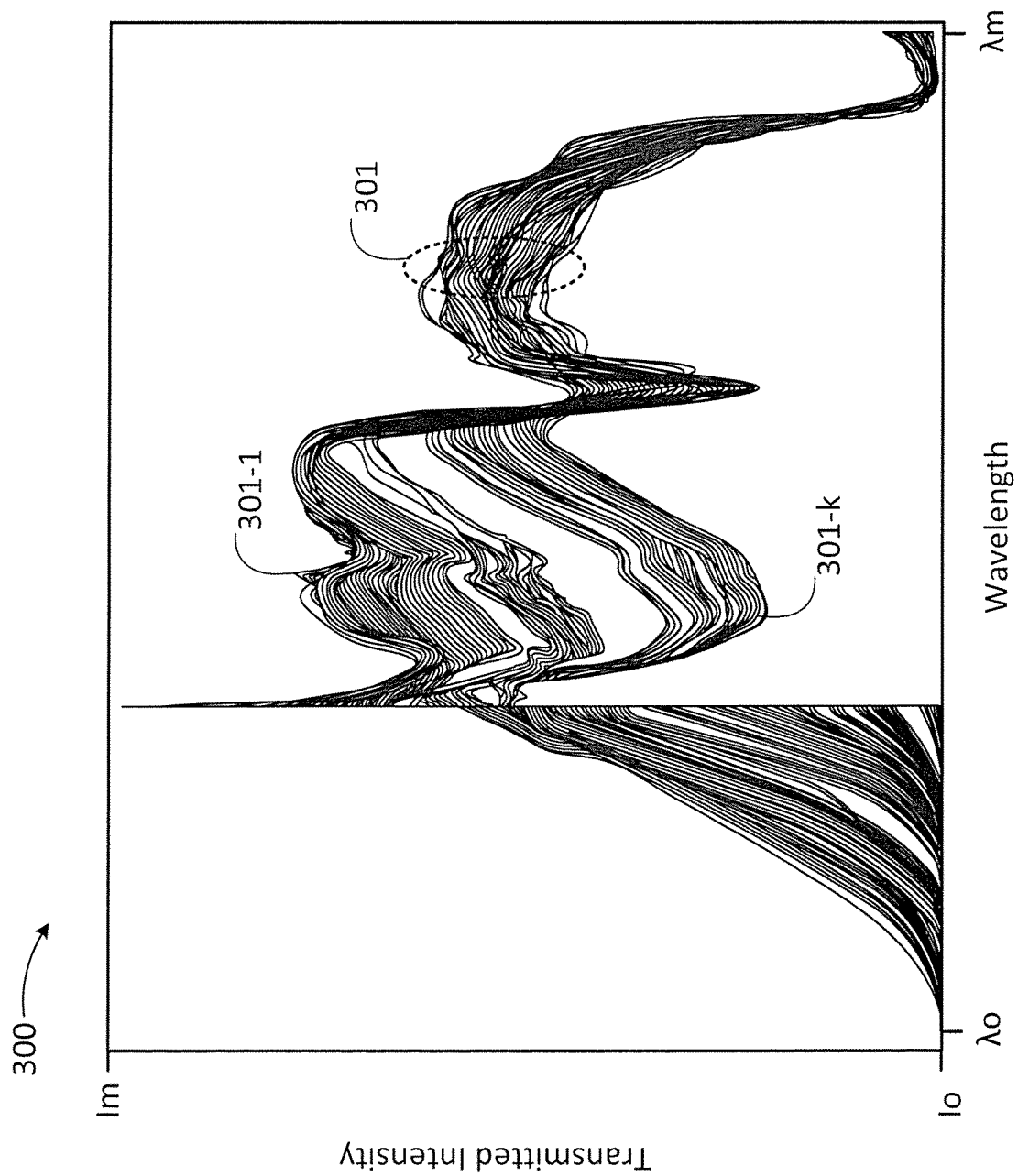
FIG. 3 illustrates a chart with spectra of a sample light from a reference fluid having varied methane concentrations.

FIG. 3 illustrates a chart 300 with spectra 301-1 . . . 301-$k$ (collectively referred to hereinafter as spectra 301) of a sample light from a reference fluid having varied methane concentrations. Chart 300 spans a minimum to a maximum transmitted intensity ($I_0$ to $I_m$) in the ordinate axis (arbitrary units) and covers a wavelength range from $\lambda_0$ at about 450 nm to about $\lambda_m$ 2500 nm (i.e., VIS-NIR), in the abscissae. The ordinates of chart 300 indicate the spectral intensity of sample light 142 impinging on optical elements 102 (FIG. 1). Accordingly, the ordinates in chart 300 are convolved with the transmission function of an optical train leading to sensing elements 102, including sapphire windows in a sample cell, a $CaF_2$ rod, band pass filters, the emission profile of light source 140 and the transmission/reflection profile of optical components 110 (FIG. 1). Spectra 301 were collected using a high-resolution spectrometer with oil samples under known pressure and temperature (e.g., a Fourier Transform Infrared spectrometer, FTIR, the 'gold standard'). Without limitation, spectra 301 includes about one-thousand seventeen (1017) light and medium oil transmission spectra obtained from an existing PVT-database with varied methane concentrations. Spectra 301 in the PVT database span a methane concentration range from 0-0.1786 grams per cubic centimeter (g/cc) of methane dissolved in the oil samples.

Figure 4:
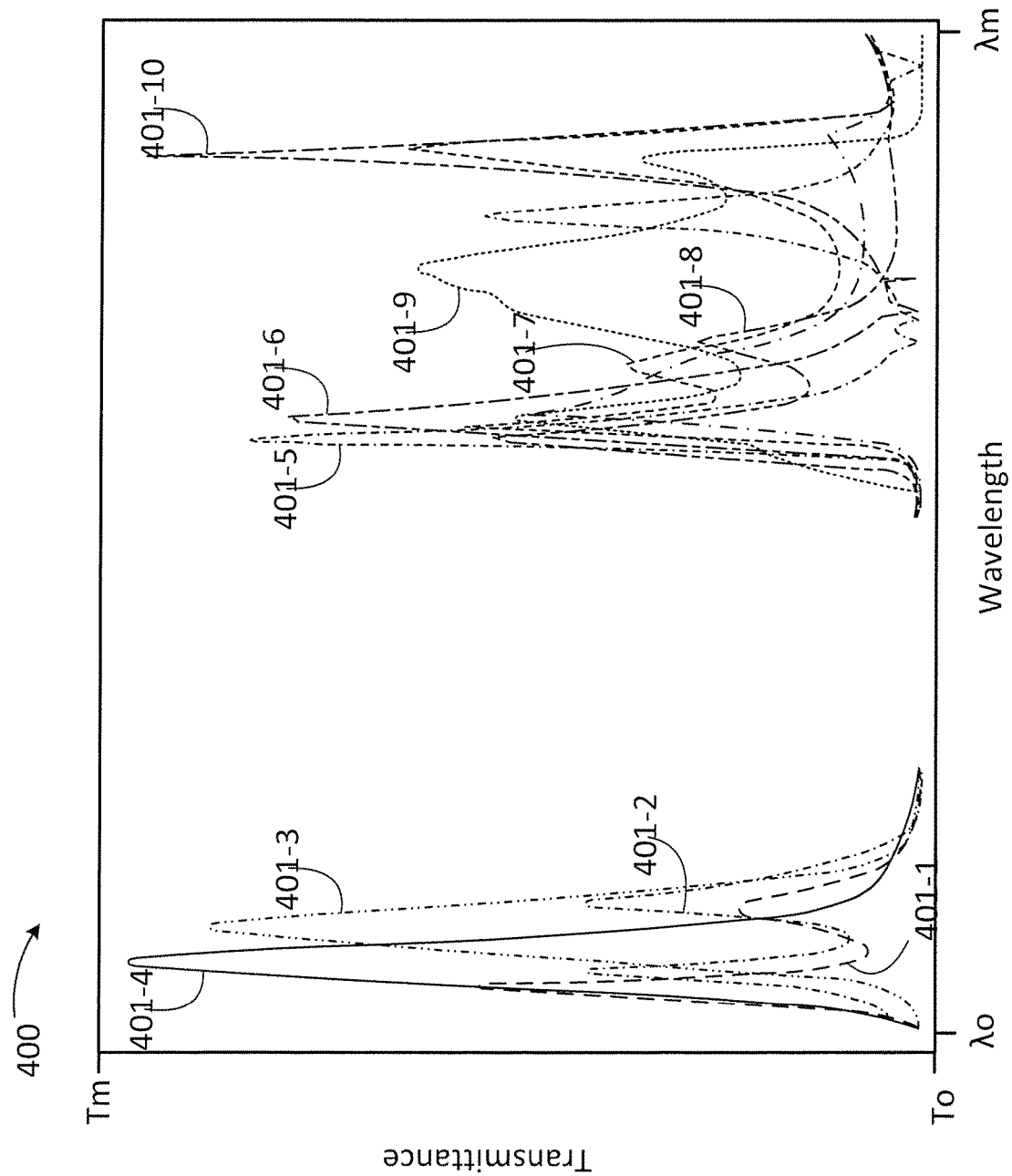
FIG. 4 illustrates a chart with transmittance spectra from a plurality of ICEs selected to measure a methane concentration from a fluid sample.

FIG. 4 illustrates a chart 400 with transmittance spectra 401-1 through 401-10 (hereinafter collectively referred to as 'spectra 401') from a plurality of optical elements selected to measure a methane concentration from a fluid sample. In some embodiments, at least one of the optical elements associated with spectra 401 may include an ICE (e.g., ICE 202, cf. FIG. 2). Further, in some embodiments the optical elements may include a broadband filter, a narrowband filter, a holographic grating, a liquid crystal, or any other optical element having a spectral transmission function as illustrated in chart 400. Chart 400 spans a minimum to a maximum transmittance ($T_0$ to $T_m$) in the ordinate axis (e.g., (0, 1)) and covers a wavelength range ($\lambda_0$, $\lambda_m$) in the abscissae (i.e., chart 300, cf. FIG. 3).

Specifically, spectra 401-1 through 401-4 include optical elements having transmission functions in the VIS-NIR range (about 450 nm-1100 nm). Further, spectra 401-5 through 401-10 include optical elements having transmission functions in the NIR range (about 1100 nm-2500 nm). Moreover, the ten sensing elements from FIG. 4 may be complemented by a temperature sensing element and a pressure sensing element (e.g., non-optical sensing elements 105-$i$ and 105-$j$, cf. FIG. 1) for a total of n=10+2=12 sensing elements. The performance of an optical computing device having the above n=12 sensing elements to measure methane concentrations may be determined using spectra 301 (cf. FIG. 3). Accordingly, an optical computing device having n=12 sensing elements for measuring methane concentration yields a partial least squares (PLS) regression with a root-mean standard error of calibration (RMSEC) of about seven percent (7.0%) relative to the highest measured methane concentration (n=12 sensing elements).

Figure 5:
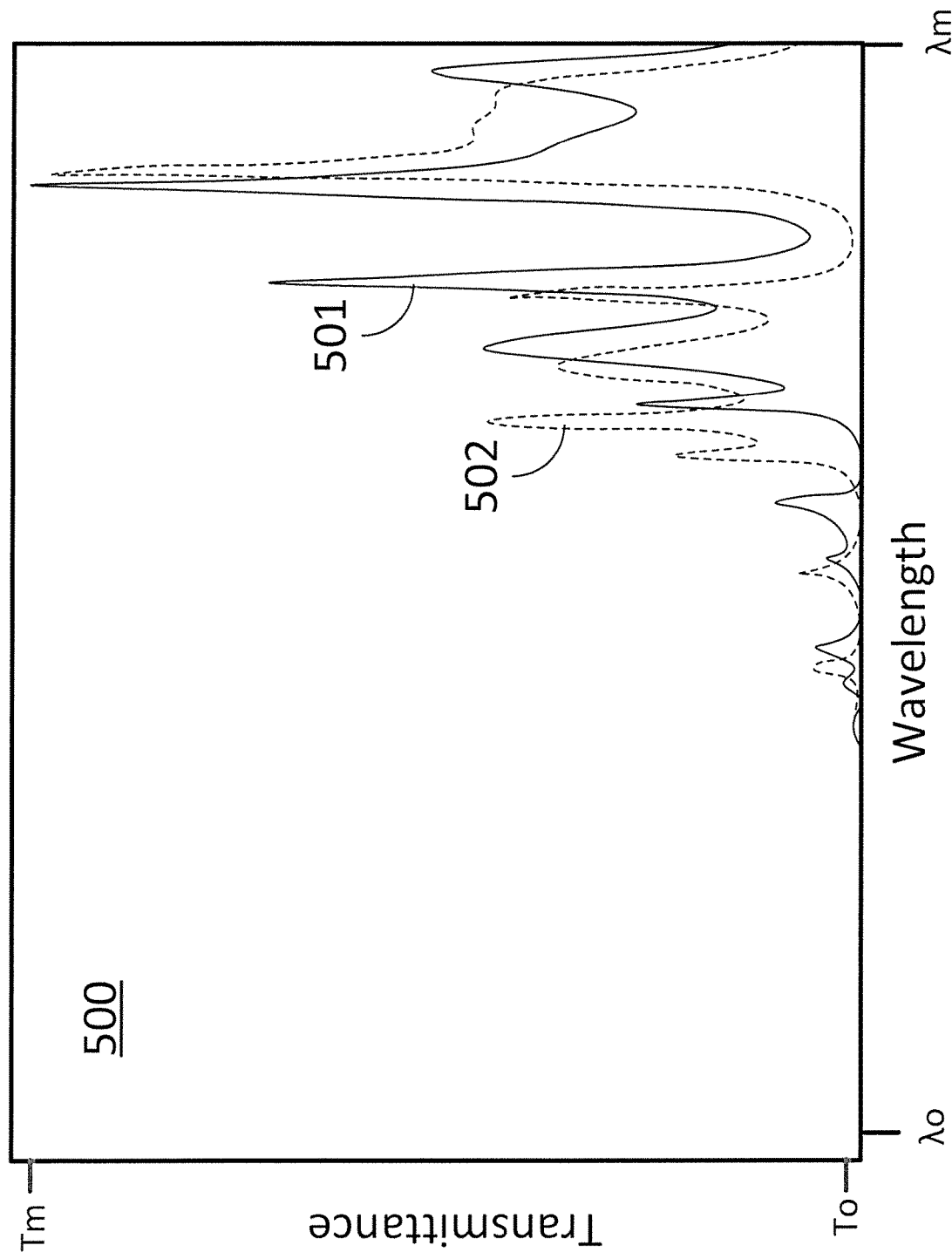
FIG. 5 illustrates a chart with an initial and a final transmittance spectra of an add-on ICE used to improve the measurement of the methane concentration from a fluid of the plurality of ICEs in FIG. 4.

FIG. 5 illustrates chart 500 with an initial spectrum 501 and a final spectrum 502 of an add-on ICE used to improve the methane concentration measurement of the optical computing device in FIG. 4 (n+1=13 sensing elements). The abscissae in chart 500 include the ($\lambda_0$, $\lambda_m$) wavelength range in the VIS-NIR range (cf. FIGS. 3-4). In some embodiments, spectrum 501 is the result of an initial add-on ICE having a random number of dielectric layers and random film stack thicknesses. Specifically, but without limitation, the initial ICE model leading to spectrum 501 is an eleven-layer film stack with alternating layers of Si and $SiO_2$ on a BK7 glass substrate (cf. FIG. 2) having initial thicknesses as listed in TABLE 1, below.

The RMSEC performance of an optical computing device having n=12+1 optical elements where the add-on optical element is the ICE leading to spectrum 501 is about 6.5% of the total methane concentration. Accordingly, the add-on ICE with spectrum 501 increases by about 0.5% the performance of the optical computing device having n=12 optical elements having spectra 401 (cf. FIG. 4), before even any optimization is performed on the layer thicknesses of the add-on ICE.

Varying layer thicknesses of the add-on ICE using an RMSEC merit function as an optimization measure leads to an add-on ICE having a spectrum 502, with final layer thicknesses as shown in TABLE 1. The optimization yields an RMSEC of about 5% methane concentration. Spectra 501 and 502 in chart 500 are presented for illustrative purposes only. In fact, according to some embodiments, the final add-on ICE may be found by directly varying the thicknesses and number of dielectric layers (cf. TABLE 1 below) and estimating the value of signal 135-13 (i.e. $135_{n+1}$ FIG. 1) from the add-on ICE (without computing the transmittance spectrum). A multivariate linear regression model is stored in memory 162 to include the 135-13 value together with the 135-1 through 135-12 values of the original optical computing device. Accordingly, optical computing device 101 provides an improved measurement of the methane concentration in an oil sample (cf. FIG. 3).

TABLE 1

| Layer # | Initial Thickness (nm) | Final Thickness (nm) |
|---|---|---|
| 1 | 348.82 | 378.43 |
| 2 | 33.10 | 5.07 |
| 3 | 609.31 | 594.38 |
| 4 | 279.89 | 314.85 |
| 5 | 46.73 | 36.74 |
| 6 | 735.50 | 704.38 |
| 7 | 527.60 | 500.51 |
| 8 | 772.83 | 766.71 |
| 9 | 399.66 | 456.58 |

TABLE 1-continued

| Layer # | Initial Thickness (nm) | Final Thickness (nm) |
|---|---|---|
| 10 | 113.53 | 185.35 |
| 11 | 756.85 | 707.66 |

Figure 6:
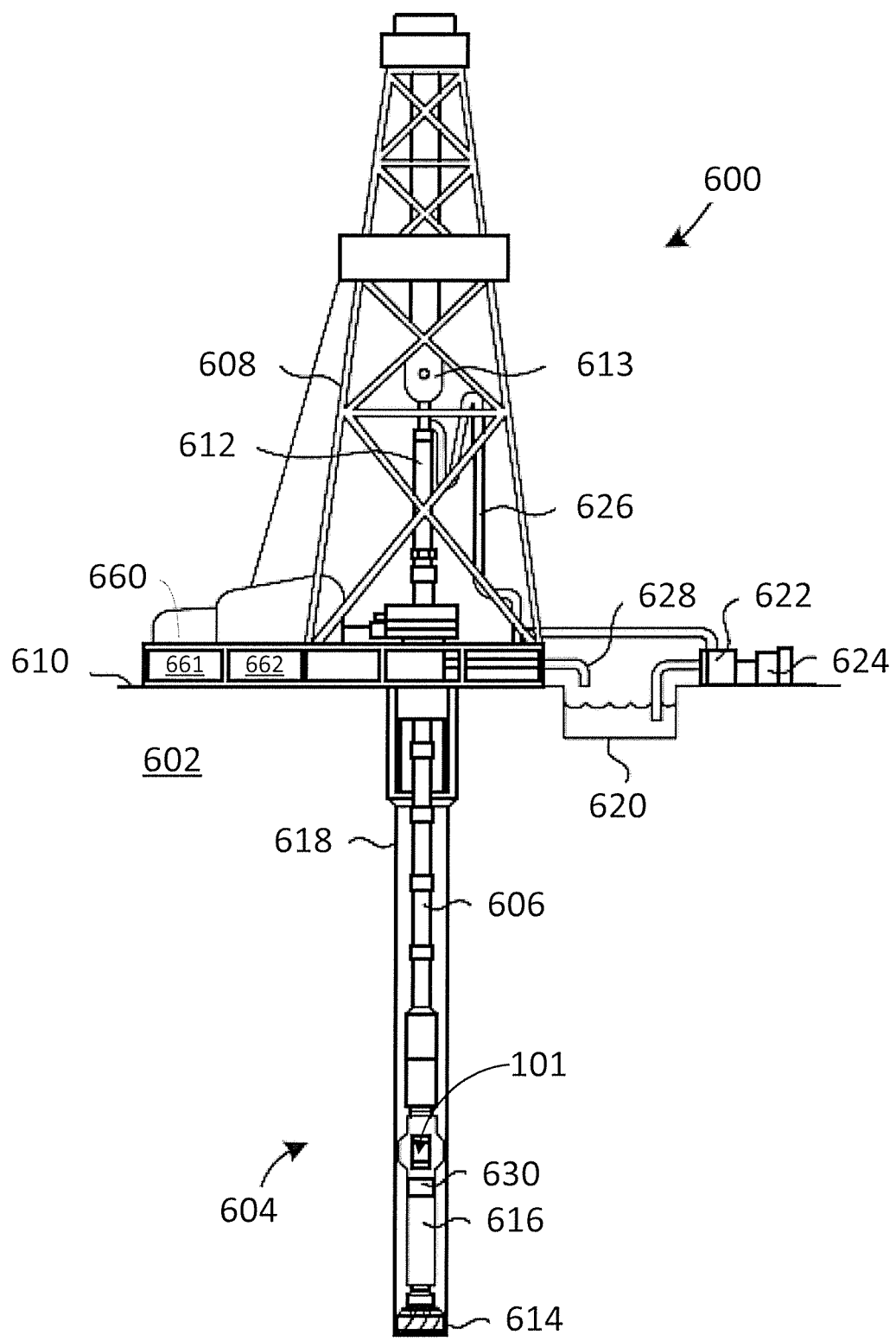
FIG. 6 illustrates a logging while drilling system including a downhole tool that uses an optical computing device having an add-on ICE.

FIG. 6 illustrates a drilling system 600 including a downhole tool 630 that uses an optical computing device 101 having an add-on ICE. Downhole tool 630 uses measurements from optical computing device 101 for modifying a drilling parameter, such as a penetration rate or a drilling direction, in a measurement-while-drilling (MWD) or a logging-while-drilling (LWD) operation, according to estimated wellbore or formation fluid properties. Drilling system 600 may be configured to drive a bottom hole assembly (BHA) 604 that is positioned or otherwise arranged at the bottom of a drill string 606 extended into the earth 602 from a derrick 608 arranged at the surface 610. The derrick 608 includes a kelly 612 and a traveling block 613 used to lower and raise the kelly 612 and a drill string 606.

The BHA 604 may include a drill bit 614 operatively coupled to a tool string 616 which may be moved axially within a wellbore 618 as attached to the drill string 606. During operation, the drill bit 614 penetrates the earth 602 and thereby creates the wellbore 618. BHA 604 provides directional control of the drill bit 614 as it advances into the earth 602. Tool string 616 can be semi-permanently mounted with various measurement tools (not shown) such as, but not limited to, measurement-while-drilling (MWD) and logging-while-drilling (LWD) tools, that may be configured to take downhole measurements of drilling conditions. In other embodiments, the measurement tools may be self-contained within the tool string 616, as shown.

Fluid or "mud" from a mud tank 620 may be pumped downhole using a mud pump 622 powered by an adjacent power source, such as a prime mover or motor 624. The mud may be pumped from the mud tank 620, through a stand pipe 626, which feeds the mud into the drill string 606 and conveys the same to drill bit 614. The mud exits one or more nozzles arranged in the drill bit 614 and in the process cools drill bit 614. After exiting drill bit 614, the mud circulates back to surface 610 via the annulus defined between wellbore 618 and drill string 606, and in the process, returns drill cuttings and debris to the surface. The cuttings and mud mixture are passed through a flow line 628 and are processed such that a cleaned mud is returned down hole through stand pipe 626 once again.

Downhole tool 630 may be controlled from the surface 610 by a controller 660 having a processor 661 and a memory 662. Accordingly, memory 662 may store commands that, when executed by processor 661, cause controller 660 to perform at least some steps in methods consistent with the present disclosure.

Figure 7:
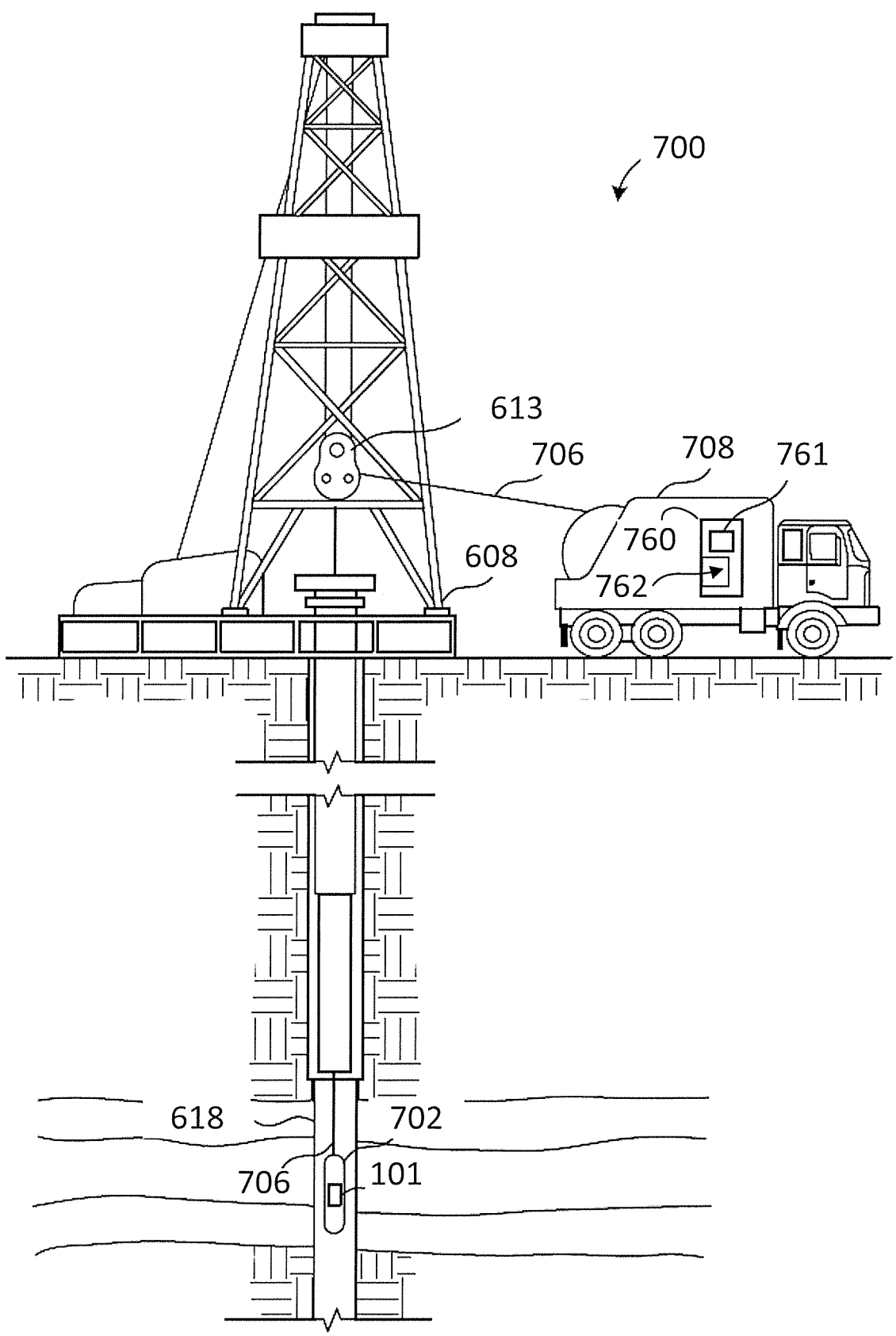
FIG. 7 illustrates a wireline system configured to measure a characteristic of a sample during formation testing and sampling with an optical computing device including an add-on ICE.

FIG. 7 illustrates a wireline system 700 configured to measure a characteristic of formation fluids during formation testing and sampling using an optical computing device 101 including an add-on ICE. System 700 may include a downhole tool 702 that forms part of a wireline logging operation that can include optical computing device 101 for determining types of formation fluids and the associated characteristics after drilling of wellbore 618 is complete. System 700 may include derrick 608 that supports traveling block 613 (cf. FIG. 6). Wireline logging tool 702, such as a probe or sonde, may be lowered by wireline or logging cable 706 into the borehole 618. Tool 702 may be lowered to the potential production zone or the region of interest in wellbore 618, and used in conjunction with other components of the formation tester such as packers and pumps to perform well testing and sampling. Optical computing device 101 may be configured to measure optical responses of the formation fluids. In some embodiments, any measurement data generated by downhole tool 702 and its associated optical computing device 101 can be real-time processed for downhole decision-making. In some embodiments, the measurement from optical computing device 101 is communicated to a surface logging facility 708 for storage, processing, and/or analysis. Logging facility 708 may be provided with electronic equipment 710, including a controller 760 having a processor 761 and a memory 762 for various types of signal processing (e.g., controllers 160, 660, processors 161, 661, and memories 162, 662, cf. FIGS. 1 and 6).

Figure 8:
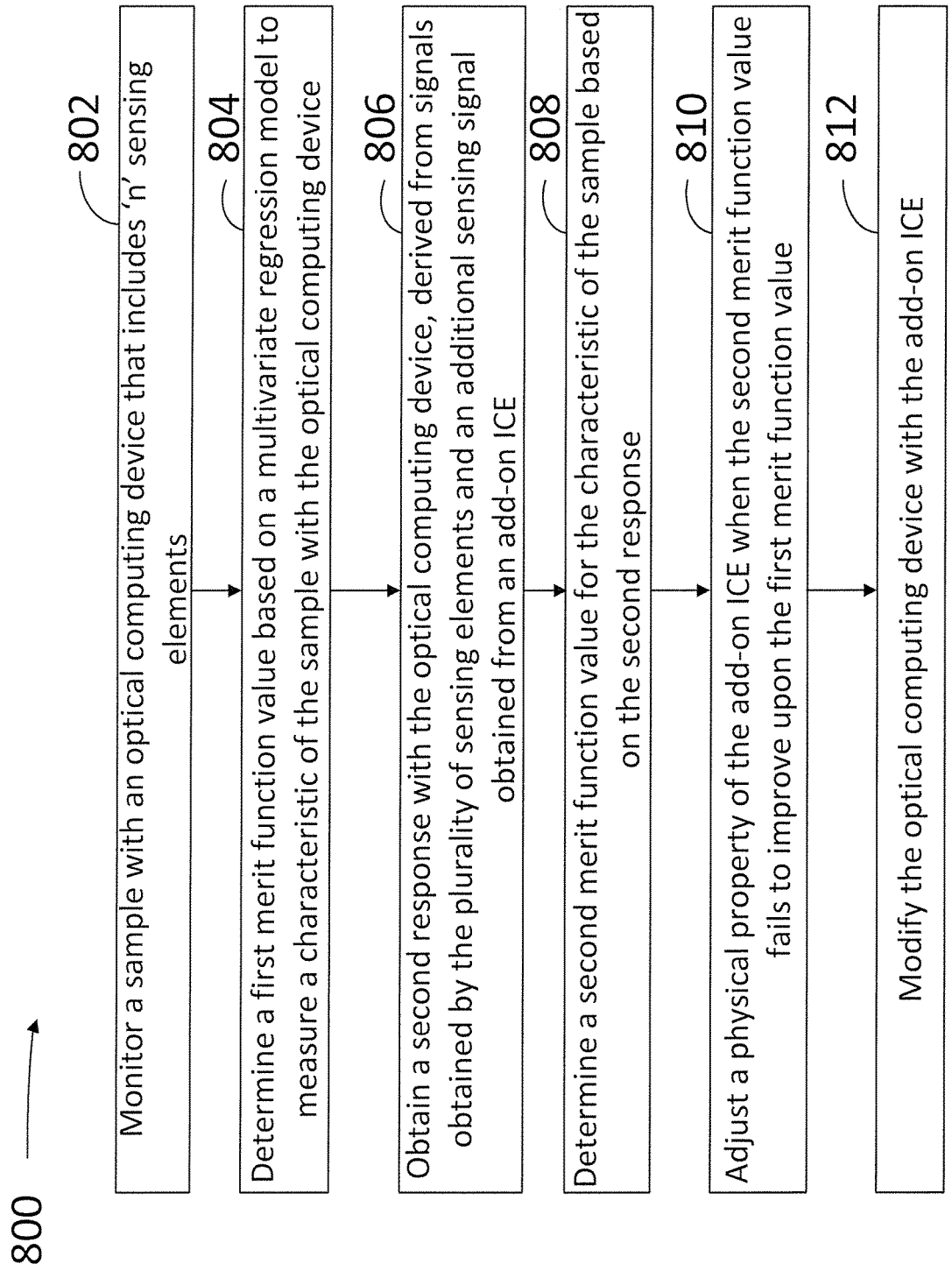
FIG. 8 illustrates a flow chart including steps in a method for improving the performance of an optical computing device with an add-on ICE.

FIG. 8 illustrates a flow chart including steps in a method 800 for improving the performance of an optical computing device with an add-on ICE. Method 800 may be performed for an optical computing device that includes a plurality of sensing elements and which is calibrated with a plurality of reference fluids from a PVT-database (e.g., optical computing device 101 sensing elements 102 and 105, and reference fluid spectra 301, cf. FIGS. 1 and 3) for determining a desired sample characteristic. In addition, method 800 may also be implemented at least partially with a computer for determining multivariate fluid characterization algorithms. Multivariate fluid characterization algorithms resulting from method 800 may be stored in a memory of a controller, (e.g., controllers 160, 660, and 760, processors 161, 661, and 761, and memories 162, 662, 762, cf. FIGS. 1, 6 and 7) to be executed by a processor (e.g., processors 161, 661, and 761 cf. FIGS. 1, 6 and 7).

Methods consistent with the present disclosure may include at least some, but not all of the steps illustrated in method 800, performed in a different sequence. Furthermore, methods consistent with the present disclosure may include at least two or more steps as in method 800 performed overlapping in time, or almost simultaneously.

Step 802 includes forming an optical computing device having a plurality of sensing elements selected to measure a characteristic of a sample. The first plurality of sensing elements may be 'n' sensing elements. In some embodiments, step 802 includes monitoring a sample with an optical computing device that includes the plurality of sensing elements. The number 'n' of pre-determined sensing elements may be any number of optical sensing elements combined with non-optical sensing elements (e.g., sensing elements 102 and non-optical sensing elements 105, cf. FIG. 1).

Step 804 includes generating a transmission function from a first add-on ICE. In some embodiments, step 804 includes generating a transmission of electromagnetic radiation through a plurality of alternating layers of material in the first add-on ICE as a function of wavelength. Step 804 may include forming the initial ICE design by randomly assigning a certain number of dielectric layers and thicknesses for the given film stack model. Further, in some embodiments step 806 includes selecting multiple random first add-on ICE models as starting points. This may facilitate finding a global minimum or maximum of the selected merit function.

Step 806 includes evaluating, with a merit function and the transmission function of the first add-on ICE, a predictive performance of a modified optical computing device according to the characteristic of the sample. In some embodiments, step 806 includes determining a predictive performance with a multivariate PLS regression model using the 'n' pre-existing sensor elements in combination with a randomly selected add-on ICE to determine the characteristic of the sample.

In some embodiments, step 806 includes determining the first merit function using a multivariate regression model to measure the characteristic of the sample with the optical computing device. Further, step 806 may include obtaining a multivariate regression model to determine a merit function value for measuring a selected characteristic of a sample using the optical computing device having 'n' pre-existing sensing elements. In some embodiments, step 806 may include selecting a root-mean standard error of calibration (RMSEC) as the merit function. Step 806 may include calculating the RMSEC of the characteristic of the sample using a PVT-database and the 'n' pre-existing sensing elements.

In step 806, the PVT-database may include multiple spectra collected for samples having a range of concentrations of a certain analyte, when the desired characteristic of the sample is the analyte concentration. Accordingly, step 806 includes developing a multivariate regression model that takes into account a detector signal from each of the pre-existing sensing elements. Step 806 may include determining a dot product of the spectrum of the sample light portion impinging on each sensing element with the transmission function of each of the 'n' sensing elements. Step 806 may include determining a predictive measurement performance (accuracy and sensitivity) of the 'n' pre-existing sensing elements including the non-optical sensing elements (e.g., determining a synthetic sensor response).

Step 806 may include determining the dot product between the transmission function of the first add-on ICE and a plurality of spectra selected from the PVT-database (e.g., determining a synthetic sensor response of the add-on ICE).

Step 808 includes modifying the first add-on ICE to improve the predictive performance of the modified optical computing device according to the merit-function and the modified transmission function of the first add-on ICE. In some embodiments, step 808 includes obtaining a second response with the modified optical computing device, including a response from the first add-on ICE. Step 808 may include evaluating the predictive performance of the modified optical computing device with the selected merit-function. Step 808 may include designing a single add-on ICE and developing a new 'n+1'-element multivariate regression model for the modified optical computing device, having a superior predictive performance relative to a multivariate regression model for the un-modified optical computing device.

Step 808 may include adjusting a physical property of the first add-on ICE when the second merit function value fails to improve upon the first merit function value. In some embodiments, step 810 includes adjusting a property of the additional ICE when the predictive performance of the modified optical computing device is not better than the predictive performance of the un-modified optical computing device. Step 808 may include iteratively regressing on layer thicknesses of the first add-on ICE until a value of the merit function for the modified optical computing device is better than a value of the merit function for the un-modified optical computing device. For example, in some embodiments step 810 includes iteratively adjusting the number and thicknesses of the layers in the add-on ICE until the RMSEC of the modified optical computing device is lower than the RMSEC of the un-modified optical computing device.

Step 808 may further include fabricating the add-on ICE based upon the new ICE design and adapting the optical computing device to include the add-on ICE. Furthermore, step 808 may include modifying a multivariate regression model stored in the memory of the controller in the optical computing device to account for the additional sensing signal.

Embodiments disclosed herein include:

A. A method, including forming an optical computing device having a plurality of sensing elements selected to measure a characteristic of a sample and generating a transmission function from a first add-on integrated computational element (ICE). The method may also include evaluating, with a merit-function and the transmission function of the first add-on ICE, a predictive performance of a modified optical computing device according to the characteristic of the sample, wherein the modified optical computing device includes the first add-on ICE in addition to the first plurality of sensing elements. Based upon the predictive performance of the modified optical computing device, the method also includes modifying the first add-on ICE to improve the predictive performance of the modified optical computing device according to the merit-function and a modified transmission function of the first add-on ICE.

B. A device, including a plurality of alternating layers of two materials having a different index of refraction. In some embodiments, a thickness of each layer and a number of the plurality of alternating layers is selected according to an intensity of a sample light transmitted through the plurality of alternating layers, the sample light being obtained by interacting an illumination light with a sample. In some embodiments, an intensity of the sample light transmitted through the plurality of alternating layers improves a merit function value for a measurement of a characteristic of the sample.

C. A system, including a light source that generates an illumination light that optically interacts with a sample to form a sample light, and a plurality of optical elements that direct a portion of the sample light to a corresponding plurality of sensing elements. In some embodiments, at least one of the plurality of sensing elements comprises a plurality of alternating layers of two materials having a different index of refraction. The system may further include an add-on integrated optical element comprising a plurality of alternating layers of two materials having a different index of refraction. In some embodiments, a thickness of each layer and a number of the plurality of alternating layers of the add-on integrated optical element are selected according to an add-on intensity of the sample light transmitted through the add-on integrated optical element. Further, in some embodiments the additional intensity improves a merit function for measuring a characteristic of the sample.

Each of embodiments A, B, and C may have one or more of the following additional elements in any combination. Element 1, wherein the merit function comprises a root mean standard deviation, the method further including determining a first merit function value by calculating the root mean standard error of calibration for the characteristic of the sample using a calibration spectra database. Element 2, wherein modifying the first add-on ICE includes one of modifying a number of alternating layers of two materials and modifying a thickness of at least one of the alternating layers of two materials in the first add-on ICE. Element 3, further including generating a multivariate regression model for the modified optical computing device to include data from the add-on ICE, and storing the modified multivariate regression model in a memory of a controller included in the optical computing device. Element 4, wherein modifying the first add-on ICE includes selecting an ICE with a random set of layers of material having random thicknesses. Element 5, wherein generating a transmission function from a first add-on ICE comprises determining an intensity of a sample light transmitted through the first add-on ICE. Element 6, wherein evaluating, with the merit-function, a predictive performance of the modified optical computing device, includes using a transmission value from the first add-on ICE in a multivariate regression model for the characteristic of the sample. Element 7, further including fabricating the modified add-on ICE to be included in the modified optical computing device. Element 8, wherein forming an optical computing device having a first plurality of sensing elements includes determining a response from at least one ICE having a broadband transmission spectrum in one of an ultraviolet spectral range, a visible spectral range, a near-infrared spectral range, or a mid-infrared spectral range. Element 9, wherein evaluating the performance of the modified optical computing device includes incorporating a response from at least one ICE having a broadband transmission spectrum in one of an ultraviolet, a visible, a near-infrared, or a mid-infrared spectral ranges, in addition to a response from the first add-on ICE.

Element 10, wherein the measurement of the characteristic of the sample includes at least a second sample light transmitted through a second plurality of alternating layers of the two materials. Element 11, wherein the merit function value is determined from electrical signals generated by sensing elements selected from the group consisting of a pressure sensor, a temperature sensor, and a densitometer. Element 12, wherein the sample light transmitted through the add-on integrated computational element includes one of an ultraviolet spectral region, a visible spectral region, a near-infrared spectral region, and a mid-infrared spectral region. Element 13, further including a controller having a memory and a processor, wherein the memory comprises commands which, when executed by the processor, cause the system to determine the characteristic of the sample. Element 14, further including a controller having a memory and a processor, wherein the processor receives electrical signals from the corresponding plurality of sensing elements and determines a value for the characteristic of the sample according to a multivariate regression algorithm stored in the memory. Element 15, further including a non-optical sensing element selected from the group consisting of a temperature sensor, a pressure sensor, and a densitometer. Element 16, wherein the plurality of sensing elements and the additional integrated computational element are included in a wireline logging tool and the characteristic of the sample is an analyte concentration in a hydrocarbon fluid. Element 17, wherein the plurality of sensing elements and the additional integrated computational element form part of a logging while drilling tool that modifies a drilling parameter according to a value of the characteristic of the sample.

Those skilled in the art will readily appreciate that the methods described herein, or large portions thereof may be automated at some point such that a computerized system may be programmed to transmit data from an optical computing device using an ICE element. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The disclosure claimed is:

1. A method, comprising:
   forming an optical computing device having a plurality of sensing elements selected to measure a characteristic of a sample;
   generating a transmission function from a first add-on integrated computational element (ICE);
   evaluating, with a merit-function and the transmission function of the first add-on ICE, a predictive performance of a modified optical computing device according to the characteristic of the sample, wherein the modified optical computing device includes the first add-on ICE in addition to the first plurality of sensing elements; and
   based upon the predictive performance of the modified optical computing device, modifying the first add-on ICE to improve the predictive performance of the modified optical computing device according to the merit-function and a modified transmission function of the first add-on ICE.

2. The method of claim 1, wherein the merit function comprises a root mean standard deviation, the method further comprising determining a first merit function value by calculating the root mean standard error of calibration for the characteristic of the sample using a calibration spectra database.

3. The method of claim 1, wherein modifying the first add-on ICE comprises one of modifying a number of alternating layers of two materials and modifying a thickness of at least one of the alternating layers of two materials in the first add-on ICE.

4. The method of claim 1, further comprising:
   generating a multivariate regression model for the modified optical computing device to include data from the add-on ICE; and
   storing the modified multivariate regression model in a memory of a controller included in the optical computing device.

5. The method of claim 1, wherein modifying the first add-on ICE comprises selecting an ICE with a random set of layers of material having random thicknesses.

6. The method of claim 1, wherein generating a transmission function from a first add-on ICE comprises determining an intensity of a sample light transmitted through the first add-on ICE.

7. The method of claim 1, wherein evaluating, with the merit-function, a predictive performance of the modified optical computing device, comprises including a transmission value from the first add-on ICE in a multivariate regression model for the characteristic of the sample.

8. The method of claim 1, further comprising fabricating the modified add-on ICE to be included in the modified optical computing device.

9. The method of claim 1, wherein forming an optical computing device having a first plurality of sensing elements comprises determining a response from at least one ICE having a broadband transmission spectrum in one of an ultraviolet spectral range, a visible spectral range, a near-infrared spectral range, or a mid-infrared spectral range.

10. The method of claim 1, wherein evaluating the performance of the modified optical computing device comprises incorporating a response from at least one ICE having a broadband transmission spectrum in one of an ultraviolet, a visible, a near-infrared, or a mid-infrared spectral ranges, in addition to a response from the first add-on ICE.

11. A device, comprising:
    a plurality of alternating layers of two materials having a different index of refraction, wherein a thickness of each layer and a number of the plurality of alternating layers is selected according to an intensity of a sample light transmitted through the plurality of alternating layers, the sample light being obtained by interacting an illumination light with a sample, and wherein an intensity of the sample light transmitted through the plurality of alternating layers improves a merit function value for a measurement of a characteristic of the sample.

12. The device of claim 11, wherein the measurement of the characteristic of the sample includes at least a second sample light transmitted through a second plurality of alternating layers of the two materials.

13. The device of claim 11, wherein the merit function value is determined from electrical signals generated by sensing elements selected from the group consisting of a pressure sensor, a temperature sensor, and a densitometer.

14. A system, comprising:
    a light source that generates an illumination light that optically interacts with a sample to form a sample light;
    a plurality of optical elements that direct a portion of the sample light to a corresponding plurality of sensing elements, wherein at least one of the plurality of sensing elements comprises a plurality of alternating layers of two materials having a different index of refraction; and
    an add-on integrated optical element comprising a plurality of alternating layers of two materials having a different index of refraction,
    wherein a thickness of each layer and a number of the plurality of alternating layers of the add-on integrated optical element are selected according to an add-on intensity of the sample light transmitted through the add-on integrated optical element, and
    wherein the add-on intensity improves a merit function for measuring a characteristic of the sample.

15. The system of claim 14, wherein the sample light transmitted through the add-on integrated optical element comprises one of an ultraviolet spectral region, a visible spectral region, a near-infrared spectral region, and a mid-infrared spectral region.

16. The system of claim 14, further comprising a controller having a memory and a processor, wherein the memory comprises commands which, when executed by the processor, cause the system to determine the characteristic of the sample.

17. The system of claim 14, further comprising a controller having a memory and a processor, wherein the processor receives electrical signals from the corresponding plurality of sensing elements and determines a value for the characteristic of the sample according to a multivariate regression algorithm stored in the memory.

18. The system of claim 14, further comprising a non-optical sensing element selected from the group consisting of a temperature sensor, a pressure sensor, and a densitometer.

19. The system of claim 14, wherein the plurality of sensing elements and the add-on integrated optical element are included in a wireline logging tool and the characteristic of the sample is an analyte concentration in a hydrocarbon fluid.

20. The system of claim 14, wherein the plurality of sensing elements and the add-on integrated optical element form part of a logging while drilling tool that modifies a drilling parameter according to a value of the characteristic of the sample.

* * * * *